(12) United States Patent
Kasaiezadeh Mahabadi et al.

(10) Patent No.: US 10,768,074 B2
(45) Date of Patent: Sep. 8, 2020

(54) VEHICLE AND METHOD FOR SUSPENSION SPRING DEGRADATION DETECTION AND FAULT TOLERANT TIRE FORCE ESTIMATION

(71) Applicant: GM Global Technology Operations LLC, Detroit, MI (US)

(72) Inventors: SeyedAlireza Kasaiezadeh Mahabadi, Shelby Township, MI (US); Seyedeh Asal Nahidi, North York (CA); James H. Holbrook, Fenton, MI (US); Jin-Jae Chen, Canton, MI (US); Bakhtiar B. Litkouhi, Washington, MI (US); Hualin Tan, Novi, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 204 days.

(21) Appl. No.: 16/116,133

(22) Filed: Aug. 29, 2018

(65) Prior Publication Data

US 2020/0072705 A1 Mar. 5, 2020

(51) Int. Cl.
*G01M 17/04* (2006.01)
*G01L 1/04* (2006.01)
*G01N 33/00* (2006.01)

(52) U.S. Cl.
CPC .............. *G01M 17/04* (2013.01); *G01L 1/04* (2013.01); *B60G 2202/10* (2013.01); *B60G 2600/08* (2013.01); *G01N 2033/0083* (2013.01); *G01N 2203/0288* (2013.01)

(58) Field of Classification Search
CPC ........ G01M 17/04; G01L 1/04; G01L 5/0057; G01L 25/00; G01N 2203/0288; G01N 2033/0083; B60G 2202/10; B60G 2600/08
See application file for complete search history.

(56) References Cited

U.S. PATENT DOCUMENTS

| 8,731,781 | B2* | 5/2014 | Prentice | B62D 35/02 |
| | | | | 701/49 |
| 9,827,957 | B2* | 11/2017 | Fahland | B60T 8/1766 |
| 9,828,044 | B2* | 11/2017 | Heil | B62D 35/005 |
| 9,937,908 | B2* | 4/2018 | Morgan | B60T 8/17551 |
| 9,950,751 | B2* | 4/2018 | Heil | B62D 35/007 |
| 10,035,549 | B2* | 7/2018 | Morgan | B62D 37/02 |
| 10,071,777 | B2* | 9/2018 | Swantick | B62D 35/007 |
| 10,246,139 | B2* | 4/2019 | Auden | B62D 35/00 |
| 2017/0088192 | A1* | 3/2017 | Auden | B62D 35/00 |

* cited by examiner

*Primary Examiner* — Freddie Kirkland, III
(74) *Attorney, Agent, or Firm* — Quinn IP Law

(57) ABSTRACT

A method of controlling an active aerodynamic system of a vehicle includes calculating a first spring force estimated value from at least one sensed vehicle handling characteristic, and a second spring force estimated value from a nominal spring characteristic curve. When a difference between the first and second spring force estimated values is equal to or greater than a spring threshold value, a nominal spring characteristic curve is adjusted to define an adjusted spring characteristic curve, and the active aerodynamic system is controlled using the adjusted spring characteristic curve. When the difference between the first and second spring force estimated values is equal to or greater than the spring threshold value, a signal may also be engaged to provide a service recommendation.

20 Claims, 3 Drawing Sheets

VEHICLE AND METHOD FOR SUSPENSION SPRING DEGRADATION DETECTION AND FAULT TOLERANT TIRE FORCE ESTIMATION

INTRODUCTION

The disclosure generally relates to a system and method of diagnosing a spring of a suspension system of a vehicle having an active aerodynamic system.

Many vehicles include a computing device that calculates a tire loading in order to control one more vehicle systems. An example of a vehicle system that requires an estimate of tire loading is an active aerodynamic system. The active aerodynamic system may include a controllable aerodynamic feature on the vehicle that may be engaged to control or adjust an amount of aerodynamic lift, downforce, and/or a lateral force generated. For example, the active aerodynamic system may include a moveable front spoiler, a moveable rear spoiler, a moveable floor pan, moveable louvers, etc. When disengaged, the active aerodynamic system maintains a constant initial position, and does not move. When engaged, the active aerodynamic system may be moved from the initial position into one or more control positions in order to control the amount of aerodynamic lift, downforce and/or aerodynamic lateral force generated. The active aerodynamic system is controlled by a computing device, which uses an estimate of tire loading to control the position of the active aerodynamic system.

The computing device uses a nominal spring characteristic curve to calculate the tire loading. The estimate of the tire loading may be used to control a vehicle system, such as but not limited to the exemplary active aerodynamic system. The nominal spring characteristic curve provides a relationship between a spring force and a spring displacement. The nominal spring characteristic curve is defined based on characteristics of the spring when manufactured. However, with use or in response to excessive loading, the characteristics of the spring may change, such that the nominal spring characteristic curve no longer accurately reflects the relationship between the spring force and the spring displacement.

SUMMARY

A method of diagnosing a spring of a suspension system of a vehicle having an active aerodynamic system is also provided. The method includes sensing at least one vehicle handling characteristic during operation of the vehicle with the active aerodynamic system disengaged. The vehicle handling characteristic is sensed with a vehicle mounted sensor. The handling characteristic of the vehicle may include at least one of an acceleration rate of the vehicle along an X axis of the vehicle, an acceleration rate of the vehicle along a Y axis of the vehicle, an acceleration rate of the vehicle along a Z axis of the vehicle, a roll rate of the vehicle, a pitch rate of the vehicle, or a vertical acceleration rate of at least one wheel of the vehicle. A computing device calculates a first spring force estimated value from the at least one vehicle handling characteristic. The computing device also calculates a second spring force estimated value from a nominal spring characteristic curve. The computing device then compares a difference between the first spring force estimated value and the second spring force estimated value to a spring threshold value, to determine if the difference is less than the spring threshold value or if the difference is equal to or greater than the spring threshold value. The computing device activates a signal to provide a service recommendation when the difference between the first spring force estimated value and the second spring force estimated value is equal to or greater than the spring threshold value.

In one embodiment of the method of diagnosing the spring of the suspension system, calculating the first spring force estimated value includes calculating a static load transfer and a dynamic load transfer at each wheel of the vehicle, calculating a damping force at each wheel of the vehicle, and calculating a relative acceleration rate between a sprung mass and an un-sprung mass at each wheel of the vehicle. The computing device then calculates the first spring force estimated value using a Kalman Filter, based on the static load transfer at each wheel of the vehicle, the dynamic load transfer at each wheel of the vehicle, the damping force at each wheel of the vehicle, and the relative acceleration rate at each wheel of the vehicle.

A method of controlling an active aerodynamic system of a vehicle is provided. The method includes sensing at least one vehicle handling characteristic during operation of the vehicle with the active aerodynamic system disengaged. The vehicle handling characteristic is sensed with a vehicle mounted sensor. A computing device calculates a first spring force estimated value from the at least one vehicle handling characteristic. The computing device calculates a second spring force estimated value from a nominal spring characteristic curve. The computing device then compares a difference between the first spring force estimated value and the second spring force estimated value to a spring threshold value, to determine if the difference is less than the spring threshold value, or if the difference is equal to or greater than the spring threshold value. When the difference between the first spring force estimated value and the second spring force estimated value is less than the spring threshold value, the computing device engages the active aerodynamic system and controls the active aerodynamic system using the nominal spring characteristic curve. When the difference between the first spring force estimated value and the second spring force estimated value is equal to or greater than the spring threshold value, the computing device adjusts the nominal spring characteristic curve to define an adjusted spring characteristic curve. The computing device may then engage the active aerodynamic system and control the active aerodynamic system using the adjusted spring characteristic curve.

In one aspect of the method of controlling the active aerodynamic system of the vehicle, the at least one handling characteristic of the vehicle includes at least one of an acceleration rate of the vehicle along an X axis of the vehicle, an acceleration rate of the vehicle along a Y axis of the vehicle, an acceleration rate of the vehicle along a Z axis of the vehicle, a roll rate of the vehicle, a pitch rate of the vehicle, or a vertical acceleration rate of at least one wheel of the vehicle.

In one aspect of the method of controlling the active aerodynamic system of the vehicle, the computing device activates a signal to provide a service recommendation when the difference between the first spring force estimated value and the second spring force estimated value is equal to or greater than the spring threshold value.

In one aspect of the method of controlling the active aerodynamic system of the vehicle, the computing device calculates the difference between the first spring force estimated value and the second spring force estimated value.

In one embodiment of the method of controlling the active aerodynamic system of the vehicle, calculating the first spring force estimated value includes calculating a static load transfer and a dynamic load transfer at each wheel of the vehicle, calculating a damping force at each wheel of the vehicle, and calculating a relative acceleration rate between a sprung mass and an un-sprung mass at each wheel of the vehicle. The computing device then uses a Kalman Filter to calculate the first spring force estimated value, based on the static load transfer at each wheel of the vehicle, the dynamic load transfer at each wheel of the vehicle, the damping force at each wheel of the vehicle, and the relative acceleration rate at each wheel of the vehicle.

In one embodiment of the method of controlling the active aerodynamic system of the vehicle, adjusting the nominal spring characteristic curve to define the adjusted spring characteristic curve includes calculating a transformation factor operable to transform the second spring force estimated value into the first spring force estimated value. The computing device may calculate the transformation factor using a Recessive Least Squares Filter, based on the first spring force estimated value and the second spring force estimated value. The transformation factor is applied to the nominal spring characteristic curve to define the adjusted spring characteristic curve.

A vehicle is also provided. The vehicle includes an active aerodynamic system that is engageable to adjust aerodynamic downforce on the vehicle. The vehicle further includes a suspension system having a spring supporting a wheel, and at least one sensor operable to sense at least one vehicle handling characteristic of the vehicle. The at least one handling characteristic of the vehicle includes at least one of an acceleration rate of the vehicle along an X axis of the vehicle, an acceleration rate of the vehicle along a Y axis of the vehicle, an acceleration rate of the vehicle along a Z axis of the vehicle, a roll rate of the vehicle, a pitch rate of the vehicle, or a vertical acceleration rate of at least one wheel of the vehicle. A computing device is disposed in communication with the active aerodynamic system and the at least one sensor. The computing device includes a processor and a memory having suspension diagnostic and control algorithm stored therein. The processor is operable to execute the suspension diagnostic and control algorithm to sense at least one vehicle handling characteristic during operation of the vehicle with the active aerodynamic system disengaged. The suspension diagnostic and control algorithm also calculates a first spring force estimated value from the at least one vehicle handling characteristic, and calculates a second spring force estimated value from a nominal spring characteristic curve stored in the memory of the computing device. The algorithm then calculates a difference between the first spring force estimated value and the second spring force estimated value, and compares the difference to a spring threshold value to determine if the difference is less than the spring threshold value or if the difference is equal to or greater than the spring threshold value. When the difference is less than the spring threshold value, the algorithm may engage and control the active aerodynamic system using the nominal spring characteristic curve. When the difference is equal to or greater than the spring threshold value, the algorithm adjusts the nominal spring characteristic curve to define an adjusted spring characteristic curve, and may then engage and control the active aerodynamic system using the adjusted spring characteristic curve.

In one embodiment of the vehicle, the processor is operable to execute the suspension diagnostic and control algorithm to activate a signal to provide a service recommendation when the difference between the first spring force estimated value and the second spring force estimated value is equal to or greater than the spring threshold value.

In one embodiment of the vehicle, the processor is operable to calculate the first spring force estimated value using a Kalman Filter, based on a static load transfer at the wheel, a dynamic load transfer at the wheel, a damping force at the wheel, and the relative acceleration rate at the wheel.

In another embodiment of the vehicle, the processor is operable to calculate a transformation factor for transforming the nominal spring characteristic curve into the adjusted spring characteristic curve, using a Recessive Least Squares Filter.

Accordingly, the current status or health of the spring of the suspensions system may be diagnosed, and a service provider may be alerted when the spring exhibits a change in performance. Additionally, when the spring exhibits a change in performance, the nominal spring characteristic curve may be adjusted to define the adjusted spring characteristic curve, which reflects the current operating characteristics of the spring. The adjusted spring characteristic curve may then be used to more accurately control the active aerodynamic system of the vehicle, based on the change in performance of the spring.

The above features and advantages and other features and advantages of the present teachings are readily apparent from the following detailed description of the best modes for carrying out the teachings when taken in connection with the accompanying drawings.

DETAILED DESCRIPTION

Those having ordinary skill in the art will recognize that terms such as "above," "below," "upward," "downward," "top," "bottom," etc., are used descriptively for the figures, and do not represent limitations on the scope of the disclosure, as defined by the appended claims. Furthermore, the teachings may be described herein in terms of functional and/or logical block components and/or various processing steps. It should be realized that such block components may be comprised of a number of hardware, software, and/or firmware components configured to perform the specified functions.

Figure 1:
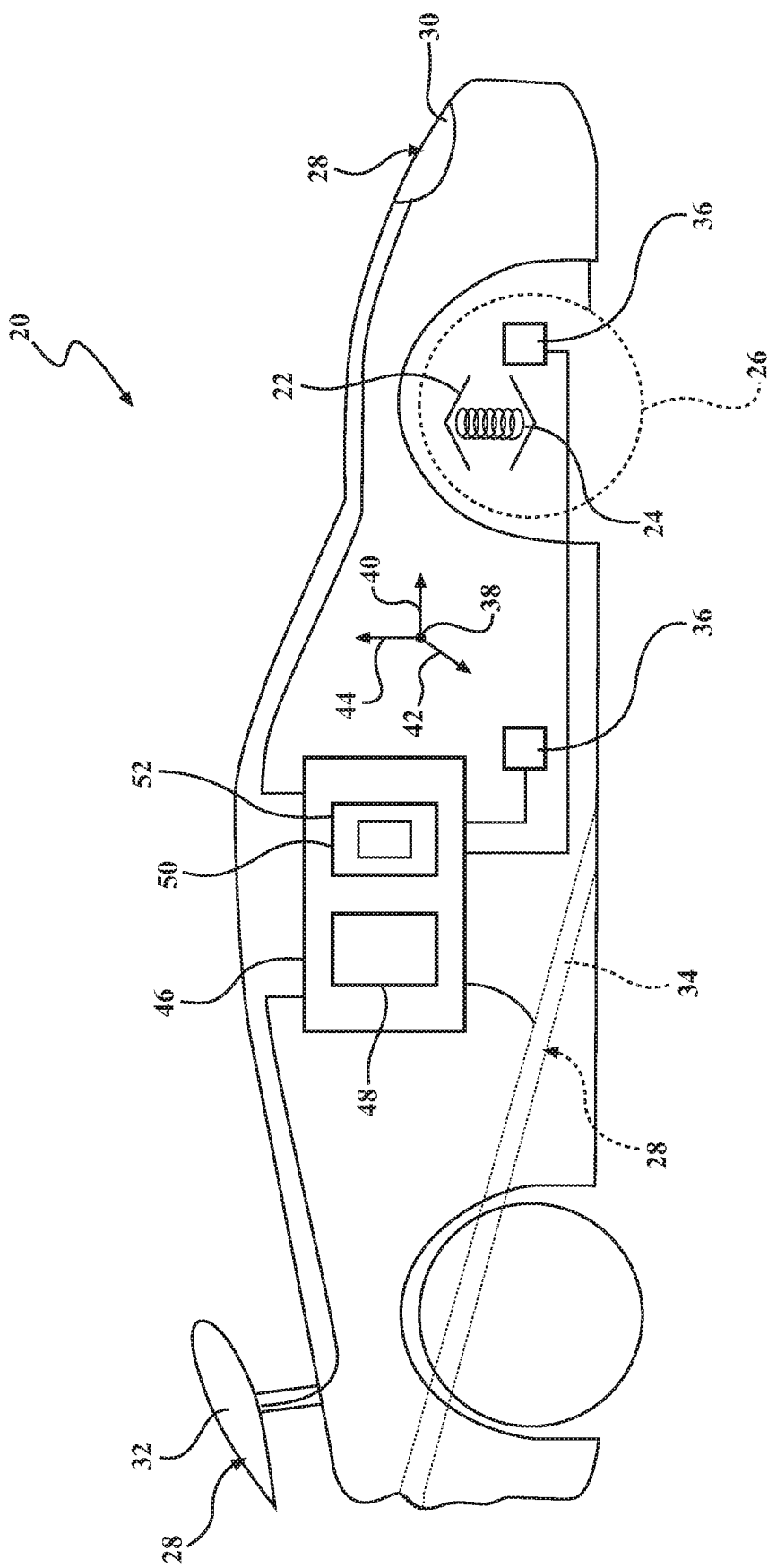
FIG. 1 is a schematic side view of a vehicle.

Referring to the FIGS., wherein like numerals indicate like parts throughout the several views, a vehicle is generally shown at 20 in FIG. 1. Referring to FIG. 1, the vehicle 20 may include a type of moveable platform including a suspension system 22 having a spring 24 that supports a wheel 26, and an active aerodynamic system 28. The specific type and configuration of the suspension system 22 is not pertinent to the teachings of this disclosure, are understood by those skilled in the art, and are therefore not described in detail herein. The spring 24 may include an elastically deformable device that is capable of storing and releasing energy. Exemplary embodiments of a spring 24 used in moveable platforms may include, but are not limited to, a coil spring, a leaf spring, or an air spring. While the written description generally describes a single wheel 26 and a single spring 24, it should be appreciated that the suspension system 22 of the vehicle 20 may include multiple wheels 26, with each wheel 26 having a respective spring 24. Furthermore, while the written description describes the suspension system 22 supporting the wheel 26, it should be appreciated that the wheel 26 may be interpreted to include some other form of surface contacting device, such as but not limited to a tracked device or a ski. Accordingly, the wheel 26 should be interpreted broadly to include other forms of ground contacting devices.

The active aerodynamic system 28 may include a controllable aerodynamic feature on the vehicle 20 that may be engaged to control or adjust an amount of aerodynamic lift, downforce, and/or a lateral force generated by air flowing across the feature. For example, the aerodynamic feature may include, but is not limited to, a moveable front spoiler 30, a moveable rear spoiler 32, a moveable floor pan 34, moveable louvers (not shown), etc. The active aerodynamic system 28 is controllable between a disengaged state, and an engaged state. When controlled into the disengaged state, the active aerodynamic system 28 maintains a constant initial position, and does not move. When controlled into the engaged state, the active aerodynamic system 28 may be moved from the initial position into one or more control positions in order to control the amount of aerodynamic lift, downforce and/or aerodynamic lateral force generated. The specific type, configuration, and operation of the active aerodynamic feature is not pertinent to the teachings of this disclosure, are understood by those skilled in the art, and are therefore not described in detail herein.

The vehicle 20 further includes one or more sensors 36 that are operable to sense data related to one or more handling characteristics of the vehicle 20. The handling characteristics of the vehicle 20 may include, but are not limited to, at least one of an acceleration rate of a center of gravity 38 of the vehicle 20 along an X axis 40 of the vehicle 20, an acceleration rate of the center of gravity 38 of the vehicle 20 along a Y axis 42 of the vehicle 20, an acceleration rate of the center of gravity 38 of the vehicle 20 along a Z axis 44 of the vehicle 20, a roll rate of the vehicle 20 about the X axis 40, a pitch rate of the vehicle 20 about the Y axis 42, or a vertical acceleration rate of at least one wheel 26 of the vehicle 20. The sensors 36 may be located at a suitable location on the vehicle 20 for the particular data being sensed. The sensors 36 may include, but are not limited to, one or more accelerometers, gyroscopes, etc. The type, kind, position, and operation of the sensors 36 are not pertinent to the teachings of this disclosure, are understood by those skilled in the art, and are therefore not described in detail herein. It should be appreciated that some or all of the handling characteristics of the vehicle 20 may be sensed at any number of the wheel/spring locations of the vehicle 20. As used herein, the X axis 40 of the vehicle 20 extends through the center of gravity 38 of the vehicle 20 and along a longitudinal centerline of the vehicle 20, between a forward end and a rearward end of the vehicle 20. The Y axis 42 of the vehicle 20 extends through the center of gravity 38 of the vehicle 20 and laterally across the vehicle 20 between a left side and a right side of the vehicle 20. The Z axis 44 of the vehicle 20 is a generally vertical axis 56 that extends through the center of gravity 38 of the vehicle 20.

A computing device 46 is disposed in communication with the active aerodynamic system 28 and the sensors 36 of the vehicle 20. The computing device 46 receives data from the sensors 36, and communicates a control signal to the active aerodynamic system 28 of the vehicle 20. The computing device 46 may be referred to as a control module, a control unit, a computer, a controller, etc. The computing device 46 controls the operation of the active aerodynamic system 28. The computing device 46 may include a computer and/or processor 48, and include software, hardware, memory 50, algorithms 52, connections, sensors 36, etc., for diagnosing the spring and for managing and controlling at least one vehicle system, such as but not limited to operation of the active aerodynamic system 28. As such, a method, described below, may be embodied as a program or algorithm operable on the computing device 46. It should be appreciated that the computing device 46 may include a device capable of analyzing data from the various sensors 36, comparing data, making the decisions required to control the operation of the active aerodynamic system 28, and executing the required tasks to control the operation of the active aerodynamic system 28.

The computing device 46 may be embodied as one or multiple digital computers or host machines each having one or more processors 48, read only memory (ROM), random access memory (RAM), electrically-programmable read only memory (EPROM), optical drives, magnetic drives, etc., a high-speed clock, analog-to-digital (A/D) circuitry, digital-to-analog (D/A) circuitry, and required input/output (I/O) circuitry, I/O devices, and communication interfaces, as well as signal conditioning and buffer electronics.

The computer-readable memory may include a non-transitory/tangible medium which participates in providing data or computer-readable instructions. Memory may be non-volatile or volatile. Non-volatile media may include, for example, optical or magnetic disks and other persistent memory. Example volatile media may include dynamic random access memory (DRAM), which may constitute a main memory. Other examples of embodiments for memory include a floppy, flexible disk, or hard disk, magnetic tape or other magnetic medium, a CD-ROM, DVD, and/or other optical medium, as well as other possible memory devices such as flash memory.

The computing device 46 includes tangible, non-transitory memory 50 on which are recorded computer-executable instructions, including a suspension diagnostic and control algorithm 52. The processor 48 of the controller is configured for executing the suspension diagnostic and control algorithm 52. The suspension diagnostic and control algorithm 52 implements a method of controlling the active aerodynamic system 28, and/or a method of diagnosing the performance of the spring 24.

Figure 2:
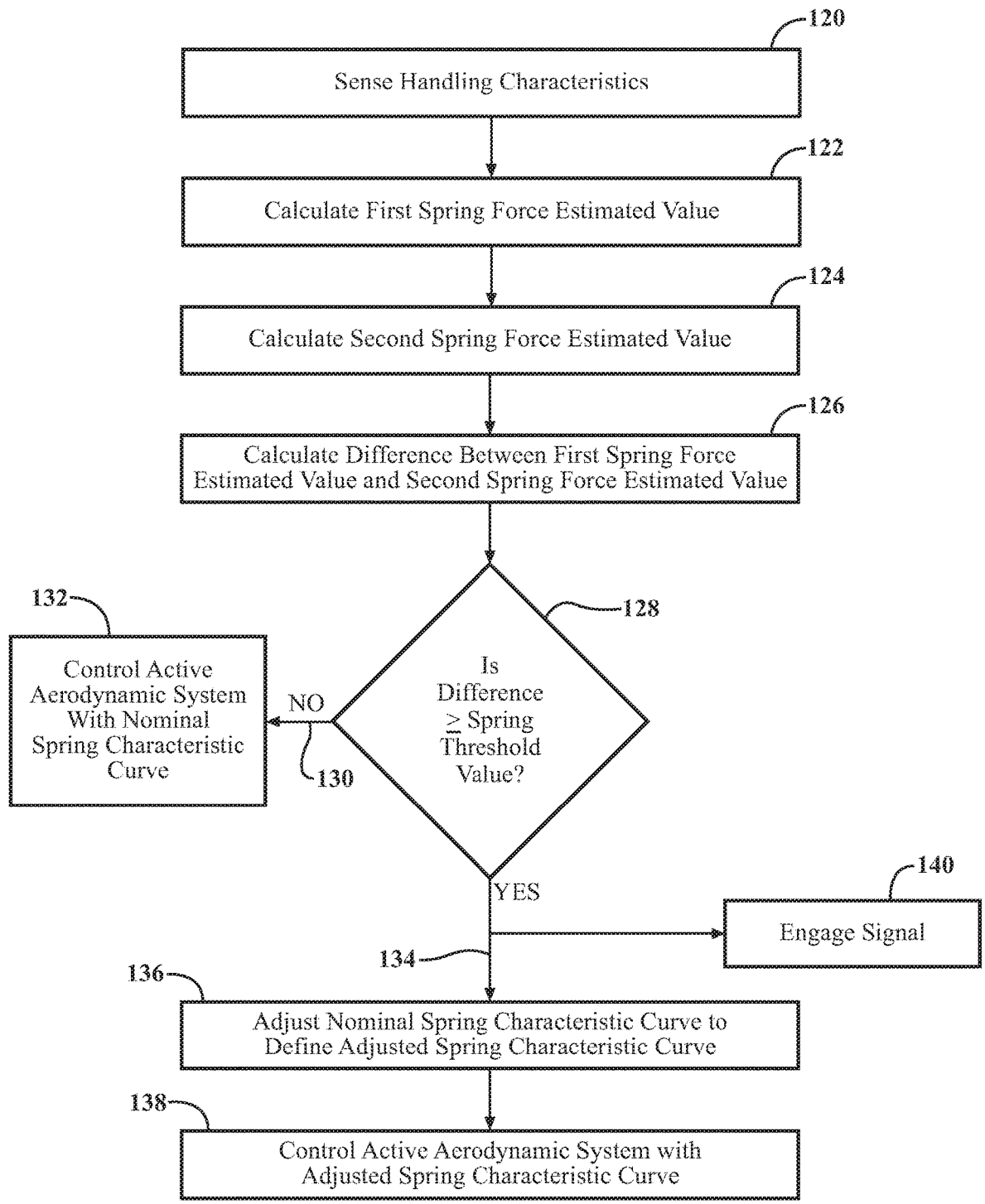
FIG. 2 is a flowchart representing a method of diagnosing a spring of the vehicle, and of controlling an active aerodynamic system of the vehicle.

Referring to FIG. 2, the method of diagnosing the performance of the spring 24 of the vehicle 20, and/or of controlling the active aerodynamic system 28 of the vehicle 20 is generally described. Although the exemplary embodiment describes the control of the active aerodynamic system 28 of the vehicle 20, it should be appreciated that the teachings of this disclosure related to diagnosing the performance of the spring 24 and adjusting a nominal spring characteristic curve 54 to define an adjusted spring characteristic curve 60 may be used to control other vehicle systems of the vehicle 20, not specifically mentioned herein.

The method includes sensing at least one vehicle 20 handling characteristic during operation of the vehicle 20 with the active aerodynamic system 28 disengaged. The step of sensing the handling characteristics of the vehicle 20 is generally indicated by box 120 in FIG. 2. The sensors 36 of the vehicle 20 gather data related to the handling characteristics of the vehicle 20 when the active aerodynamic system 28 is disengaged, and therefore not being actively moved between different positions. As noted above, the handling characteristics of the vehicle 20 may include, but are not limited to, at least one of the acceleration rate of the center of gravity 38 of the vehicle 20 along the X axis 40 of the vehicle 20, the acceleration rate of the center of gravity 38 of the vehicle 20 along the Y axis 42 of the vehicle 20, the acceleration rate of the center of gravity 38 of the vehicle 20 along the Z axis 44 of the vehicle 20, the roll rate of the vehicle 20 about the X axis 40, the pitch rate of the vehicle 20 about the Y axis 42, or a vertical acceleration rate of the wheel 26.

The computing device 46 uses the sensed handling characteristics of the vehicle 20 to calculate a first spring force estimated value. The step of calculating the first spring force estimated value is generally indicated by box 122 in FIG. 2. Accordingly, the sensed handling characteristics may include a combination of characteristics that enable the computing device 46 to calculate the first spring force estimated value, whether described herein or not. The first spring force estimated value is a calculated value of the amount of spring force generated by the spring 24 at the moment the handling characteristics were sensed. It should be appreciated that the first spring force estimated value may be calculated for each spring 24 of the vehicle 20.

The first spring force estimated value may be calculated in a suitable manner. For example, the exemplary embodiment described herein includes calculating a static load transfer and a dynamic load transfer at the wheel 26, calculating a damping force at the wheel 26, and calculating a relative acceleration rate between a sprung mass and an un-sprung mass at the wheel 26. As noted above, the first spring force estimated value may be calculated for each wheel 26. Accordingly, the static load transfer and the dynamic load transfer, the damping force, and the relative acceleration may be calculated respectively for each wheel 26 of the vehicle 20. The computing device 46 may then calculate the first spring force estimated value using a filter, such as but not limited to a Kalman Filter, based on the static load transfer at each wheel 26 of the vehicle 20, the dynamic load transfer at each wheel 26 of the vehicle 20, the damping force at each wheel 26 of the vehicle 20, and the relative acceleration rate at each wheel 26 of the vehicle 20.

The static load transfer at each wheel 26 of the vehicle 20, the dynamic load transfer at each wheel 26 of the vehicle 20, the damping force at each wheel 26 of the vehicle 20, and the relative acceleration rate between the sprung mass and the un-sprung mass at each wheel 26 of the vehicle 20 may be calculated in a suitable manner. Exemplary processes used to calculate the static load transfer, the dynamic load transfer, the damping force, and the relative acceleration rate between the sprung mass and the un-spring 24 mass are understood by those skilled in the art, and are therefore not described in detail herein.

Figure 3:
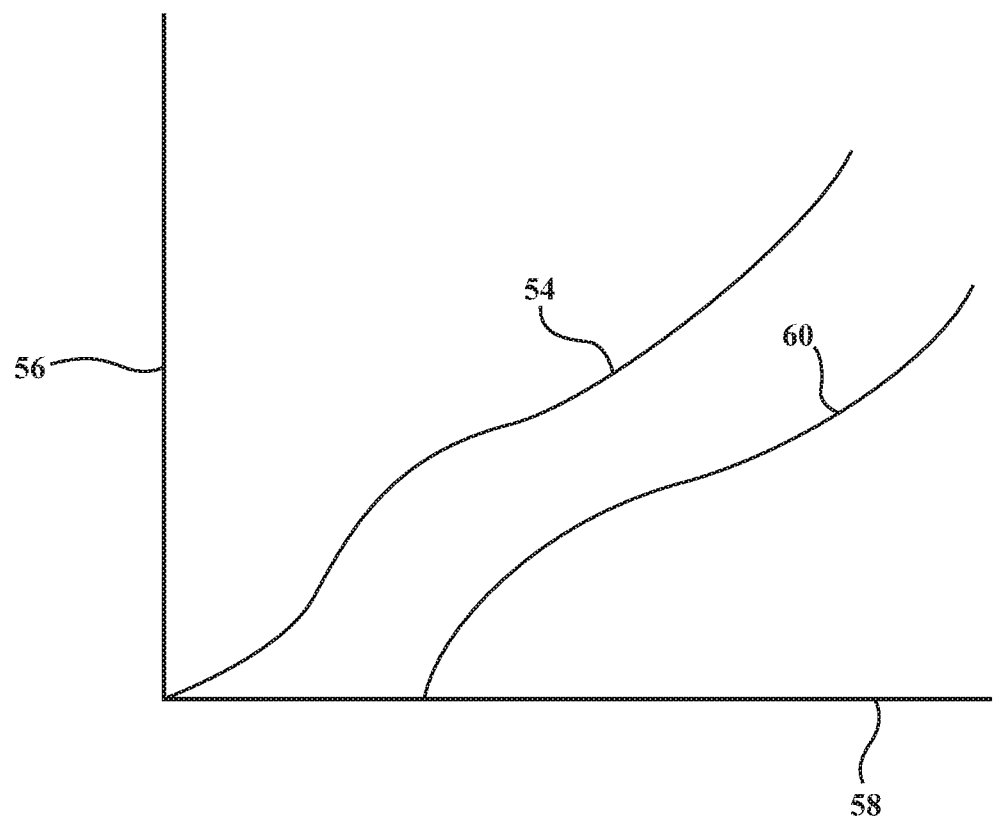
FIG. 3 is a graph showing a nominal spring characteristic curve and an adjusted spring characteristic curve.

The computing device 46 further calculates a second spring force estimated value from a nominal spring characteristic curve 54. The step of calculating the second spring force estimated value is generally indicated by box 124 in FIG. 2. The nominal spring characteristic curve 54 is stored in the memory 50 of the computing device 46. FIG. 3, shows the relationship between a force of the spring 24 along a vertical axis 56, relative to a displacement of the spring 24 along a horizontal axis 58. The nominal spring characteristic curve is generally shown by the line 54. The nominal spring characteristic curve 54 is used by the computing device 46 to calculate a tire force, which is then used to control the position of the active aerodynamic system 28. The manner in which the computing device 46 calculates the second spring force estimated value from the nominal spring characteristic curve 54 is understood by those skilled in the art, and is therefore not described in detail herein. The nominal spring characteristic curve 54 is initially defined to relate the force of the spring 24 to the displacement of the spring 24, when the spring 24 is new. Accordingly, the nominal spring characteristic curve 54 represents an intended or design relationship between force and displacement of the spring 24. As such, under normal operating circumstances, the spring 24 operates as described by the nominal spring characteristic curve 54.

Because the first spring force estimated value is calculated from sensed handling characteristics of the vehicle 20, the first spring force estimated value represents an actual or current functionality of the spring 24. Because the second spring force estimated value is calculated using the nominal spring characteristic curve 54, the second spring force estimated value represents the intended or expected functionality of the spring 24 as designed.

The computing device 46 may then calculate a difference between the first spring force estimated value and the second spring force estimated value. The step of calculating the difference is generally indicated by box 126 in FIG. 2. The difference between the first spring force estimated value and the second spring force estimated value may be calculated in a suitable manner. For example, the computing device 46 may subtract the first spring force estimated value from the second spring force estimated value to calculate the difference. In some embodiments, the computing device 46 may then take the absolute value of the difference so that the difference is expressed as a positive value.

The computing device 46 then compares the difference between the first spring force estimated value and the second spring force estimated value to a spring threshold value, to determine if the difference is less than the spring threshold value, or if the difference is equal to or greater than the spring threshold value. The step of comparing the difference to the spring threshold value is generally indicated by box 128 in FIG. 2. The spring threshold value is a pre-defined value that indicates excessive deviation of performance of the spring 24 relative to the intended performance. If the difference is expressed as an absolute value, then the spring threshold value may be defined as a single positive value, in which the absolute value of the difference is either less than the spring threshold value, equal to the spring threshold value, or greater than the spring threshold value. If the difference is expressed as either a negative value or a positive value, then the spring threshold value may be defined as a range. As such, the difference may be considered greater than the spring threshold value if the difference is outside of the range of the spring threshold value. It should be appreciated that the specific manner in which the difference and the spring threshold value are expressed and/or compared to each other may vary from the exemplary embodiments disclosed herein.

When the difference between the first spring force estimated value and the second spring force estimated value is less than the spring threshold value, generally indicated at 130, the computing device 46 may determine that the spring 24 is operating as intended and as described by the nominal spring characteristic curve 54. As such, the computing device 46 may engage the active aerodynamic system 28 and control the active aerodynamic system 28 using the nominal spring characteristic curve 54. It should be appreciated that other vehicle systems may also be controlled using the nominal spring characteristic curve 54 as well. The step of controlling the active aerodynamic system 28 using the nominal spring characteristic curve 54 is generally indicated by box 132 in FIG. 2.

When the difference between the first spring force estimated value and the second spring force estimated value is equal to or greater than the spring threshold value, generally indicated at 134, the computing device 46 may determine that the spring 24 is not operating as intended, and that the nominal spring characteristic curve 54 no longer accurately reflects the current performance of the spring 24. As such, when the difference between the first spring force estimated value and the second spring force estimated value is equal to or greater than the spring threshold value, the computing device 46 may adjust the nominal spring characteristic curve 54 to define an adjusted spring characteristic curve 60. The step of adjusting the nominal spring characteristic curve 54 to define the adjusted spring characteristic curve 60 is generally indicated by box 136 in FIG. 2. Referring to FIG. 3, the adjusted spring characteristic curve is generally indicated by line 60.

The computing device 46 may adjust the nominal spring characteristic curve 54 to define the adjusted spring characteristic curve 60 in a suitable manner. For example, the computing device 46 may calculate a transformation factor that is operable to transform the second spring force estimated value into the first spring force estimated value. The transformation factor may be calculated to adjust the nominal spring characteristic curve 54 in one or more dimensions. For example, the transformation factor may move the nominal spring characteristic curve 54 along one or both of the vertical axis 56 and the horizontal axis 58, may scale the nominal spring characteristic curve 54 along one or both of the vertical axis 56 and the horizontal axis 58, and/or may rotate the nominal spring characteristic curve 54 about a point. The computing device 46 may calculate the transformation factor in a suitable manner. For example, the computing device 46 may use a filter, such as but not limited to, a Recessive Least Squares Filter, to calculate the transformation factor based on the first spring force estimated value and the second spring force estimated value. The transformation factor may then be applied to the nominal spring characteristic curve 54 to define the adjusted spring characteristic curve 60.

The specific process used to adjust the nominal spring characteristic curve 54 may differ from the exemplary embodiment described herein. Many mathematical processes are understood by those skilled in the art that are suitable for adjusting a curve to best fit one or more points. Accordingly, the specific process used to adjust the nominal spring characteristic curve 54 to define the adjusted spring characteristic curve 60 should not be limited to the exemplary embodiment described herein.

When the difference between the first spring force estimated value and the second spring force estimated value is equal to or greater than the spring threshold value, and after the computing device 46 has adjusted the nominal spring characteristic curve 54 to define the adjusted spring characteristic curve 60, the computing device 46 may then engage the active aerodynamic system 28 of the vehicle 20, and control the active aerodynamic system 28 using the adjusted spring characteristic curve 60. The step of controlling the active aerodynamic system 28 using the adjusted spring characteristic curve 60 is generally indicated by box 138 in FIG. 2. Because the adjusted spring characteristic curve 60 reflects the current functionally of the spring 24, the computing device 46 may more accurately calculate the tire force for controlling the active aerodynamic system 28 for the current performance of the spring 24. It should be appreciated that the adjusted spring characteristic curve 60 may be used to control other vehicle systems as well. As such, the process described herein improves the functionality of the active aerodynamic system 28 (or other vehicle system requiring an estimated tire loading) when the spring 24 performance deviates from the nominal spring characteristic curve 54.

Additionally, as noted above, when the difference between the first spring force estimated value and the second spring force estimated value is equal to or greater than the spring threshold value, generally indicated at 134, the computing device 46 may determine that the spring 24 is no longer functioning as intended or designed, and may require service. Therefore, when the difference between the first spring force estimated value and the second spring force estimated value is equal to or greater than the spring threshold value, the computing device 46 may engage or activate a signal 62 to provide a service request or recommendation. The step of engaging or activating the signal 62 is generally indicated by box 140 in FIG. 2. The signal 62 may include, but is not limited to, a warning light, an audible warning, a transmitted signal to a remote service provider, or some other device capable of notifying a service provider that the spring 24 may require maintenance.

The detailed description and the drawings or figures are supportive and descriptive of the disclosure, but the scope of the disclosure is defined solely by the claims. While some of the best modes and other embodiments for carrying out the claimed teachings have been described in detail, various alternative designs and embodiments exist for practicing the disclosure defined in the appended claims.

What is claimed is:

1. A method of diagnosing a spring of a suspension system of a vehicle having an active aerodynamic system, the method comprising:
   sensing at least one vehicle handling characteristic during operation of the vehicle with the active aerodynamic system disengaged, with a vehicle mounted sensor;
   calculating a first spring force estimated value from the at least one vehicle handling characteristic, with a computing device;
   calculating a second spring force estimated value from a nominal spring characteristic curve, with the computing device;
   comparing a difference between the first spring force estimated value and the second spring force estimated value to a spring threshold value, to determine if the difference is less than the spring threshold value or if the difference is equal to or greater than the spring threshold value; and
   activating a signal, with the computing device, to provide a service recommendation when the difference between the first spring force estimated value and the second spring force estimated value is equal to or greater than the spring threshold value.

2. The method set forth in claim 1, wherein calculating the first spring force estimated value includes calculating a static load transfer and a dynamic load transfer at each wheel of the vehicle.

3. The method set forth in claim 2, wherein calculating the first spring force estimated value includes calculating a damping force at each wheel of the vehicle.

4. The method set forth in claim 3, wherein calculating the first spring force estimated value includes calculating a relative acceleration rate between a sprung mass and an un-sprung mass at each wheel of the vehicle.

5. The method set forth in claim 4, wherein calculating the first spring force estimated value is further defined as calculating the first spring force estimated value using a Kalman Filter, based on the static load transfer at each wheel of the vehicle, the dynamic load transfer at each wheel of the vehicle, the damping force at each wheel of the vehicle, and the relative acceleration rate at each wheel of the vehicle.

6. The method set forth in claim 1, wherein the at least one handling characteristic of the vehicle includes at least one of an acceleration rate of the vehicle along an X axis of the vehicle, an acceleration rate of the vehicle along a Y axis of the vehicle, an acceleration rate of the vehicle along a Z axis of the vehicle, a roll rate of the vehicle, a pitch rate of the vehicle, or a vertical acceleration rate of at least one wheel of the vehicle.

7. The method set forth in claim 1, further comprising:
engaging and controlling the active aerodynamic system with the computing device, using the nominal spring characteristic curve, when the difference between the first spring force estimated value and the second spring force estimated value is less than the spring threshold value;
adjusting the nominal spring characteristic curve to define an adjusted spring characteristic curve, with the computing device, when the difference between the first spring force estimated value and the second spring force estimated value is equal to or greater than the spring threshold value; and
engaging and controlling the active aerodynamic system with the computing device, using the adjusted spring characteristic curve, when the difference between the first spring force estimated value and the second spring force estimated value is equal to or greater than the spring threshold value.

8. The method set forth in claim 7, wherein adjusting the nominal spring characteristic curve to define the adjusted spring characteristic curve includes calculating a transformation factor operable to transform the second spring force estimated value into the first spring force estimated value.

9. A method of controlling an active aerodynamic system of a vehicle, the method comprising:
sensing at least one vehicle handling characteristic during operation of the vehicle with the active aerodynamic system disengaged, with a vehicle mounted sensor, wherein the at least one handling characteristic of the vehicle includes at least one of an acceleration rate of the vehicle along an X axis of the vehicle, an acceleration rate of the vehicle along a Y axis of the vehicle, an acceleration rate of the vehicle along a Z axis of the vehicle, a roll rate of the vehicle, a pitch rate of the vehicle, or a vertical acceleration rate of at least one wheel of the vehicle;
calculating a first spring force estimated value from the at least one vehicle handling characteristic, with a computing device;
calculating a second spring force estimated value from a nominal spring characteristic curve, with the computing device;
comparing a difference between the first spring force estimated value and the second spring force estimated value to a spring threshold value, to determine if the difference is less than the spring threshold value or if the difference is equal to or greater than the spring threshold value;
engaging and controlling the active aerodynamic system with the computing device, using the nominal spring characteristic curve, when the difference between the first spring force estimated value and the second spring force estimated value is less than the spring threshold value;
adjusting the nominal spring characteristic curve to define an adjusted spring characteristic curve, with the computing device, when the difference between the first spring force estimated value and the second spring force estimated value is equal to or greater than the spring threshold value; and
engaging and controlling the active aerodynamic system with the computing device, using the adjusted spring characteristic curve, when the difference between the first spring force estimated value and the second spring force estimated value is equal to or greater than the spring threshold value.

10. The method set forth in claim 9, further comprising activating a signal, with the computing device, to provide a service recommendation when the difference between the first spring force estimated value and the second spring force estimated value is equal to or greater than the spring threshold value.

11. The method set forth in claim 9, wherein calculating the first spring force estimated value includes calculating a static load transfer and a dynamic load transfer at each wheel of the vehicle.

12. The method set forth in claim 11, wherein calculating the first spring force estimated value includes calculating a damping force at each wheel of the vehicle.

13. The method set forth in claim 12, wherein calculating the first spring force estimated value includes calculating a relative acceleration rate between a sprung mass and an un-sprung mass at each wheel of the vehicle.

14. The method set forth in claim 13, wherein calculating the first spring force estimated value is further defined as calculating the first spring force estimated value using a Kalman Filter, based on the static load transfer at each wheel of the vehicle, the dynamic load transfer at each wheel of the vehicle, the damping force at each wheel of the vehicle, and the relative acceleration rate at each wheel of the vehicle.

15. The method set forth in claim 9, wherein adjusting the nominal spring characteristic curve to define the adjusted spring characteristic curve includes calculating a transformation factor operable to transform the second spring force estimated value into the first spring force estimated value.

16. A vehicle comprising:
an active aerodynamic system engageable to adjust aerodynamic downforce on the vehicle;
a suspension system having a spring supporting a wheel;
at least one sensor operable to sense at least one vehicle handling characteristic of the vehicle, wherein the at least one handling characteristic of the vehicle includes at least one of an acceleration rate of the vehicle along an X axis of the vehicle, an acceleration rate of the vehicle along a Y axis of the vehicle, an acceleration rate of the vehicle along a Z axis of the vehicle, a roll rate of the vehicle, a pitch rate of the vehicle, or a vertical acceleration rate of at least one wheel of the vehicle;
a computing device in communication with the active aerodynamic system and the at least one sensor, wherein the computing device includes a processor and a memory having suspension diagnostic and control algorithm stored therein, and wherein the processor is operable to execute the suspension diagnostic and control algorithm to:
sense at least one vehicle handling characteristic during operation of the vehicle with the active aerodynamic system disengaged;
calculate a first spring force estimated value from the at least one vehicle handling characteristic;

calculate a second spring force estimated value from a nominal spring characteristic curve stored in the memory of the computing device;
calculate a difference between the first spring force estimated value and the second spring force estimated value;
compare the difference to a spring threshold value to determine if the difference is less than the spring threshold value or if the difference is equal to or greater than the spring threshold value; and
activate a signal to provide a service recommendation when the difference is equal to or greater than the spring threshold value.

17. The vehicle set forth in claim 16, wherein the processor is operable to calculate the first spring force estimated value using a Kalman Filter, based on a static load transfer at the wheel, a dynamic load transfer at the wheel, a damping force at the wheel, and a relative acceleration rate at the wheel.

18. The vehicle set forth in claim 16, wherein the processor is operable to execute the suspension diagnostic and control algorithm to engage and control the active aerodynamic system using the nominal spring characteristic curve when the difference is less than the spring threshold value.

19. The vehicle set forth in claim 16, wherein the processor is operable to execute the suspension diagnostic and control algorithm to:
adjust the nominal spring characteristic curve to define an adjusted spring characteristic curve when the difference is equal to or greater than the spring threshold value; and
engage and control the active aerodynamic system using the adjusted spring characteristic curve when the difference is equal to or greater than the spring threshold value.

20. The vehicle set forth in claim 19, wherein the processor is operable to calculate a transformation factor for adjusting the nominal spring characteristic curve into the adjusted spring characteristic curve using a Recessive Least Squares Filter.

* * * * *